(12) United States Patent
Kahlman

(10) Patent No.: US 9,766,231 B2
(45) Date of Patent: Sep. 19, 2017

(54) MAGNETIC BEAD ACTUATION USING FEEDBACK FOR FTIR BIOSENSOR

(71) Applicant: KONINKLIJKE PHILIPS N.V., Eindhoven (NL)

(72) Inventor: Josephus Arnoldus Henricus Maria Kahlman, Tilburg (NL)

(73) Assignee: KONINKLIJKE PHIIPS N.V., Eindhoven (NL)

( * ) Notice: Subject to any disclaimer, the term of this patent is extended or adjusted under 35 U.S.C. 154(b) by 158 days.

(21) Appl. No.: 14/453,005

(22) Filed: Aug. 6, 2014

(65) Prior Publication Data

US 2014/0348705 A1 Nov. 27, 2014

Related U.S. Application Data

(62) Division of application No. 12/865,864, filed as application No. PCT/IB2009/050396 on Feb. 2, 2009, now Pat. No. 8,822,227.

(30) Foreign Application Priority Data

Feb. 6, 2008 (EP) .................................... 08101328

(51) Int. Cl.
*G01N 21/00* (2006.01)
*G01N 33/543* (2006.01)
*G01N 27/74* (2006.01)
*G01N 21/552* (2014.01)
*G01N 35/00* (2006.01)

(52) U.S. Cl.
CPC ..... *G01N 33/54333* (2013.01); *G01N 27/745* (2013.01); *G01N 33/54373* (2013.01); *G01N 21/552* (2013.01); *G01N 35/0098* (2013.01)

(58) Field of Classification Search
None
See application file for complete search history.

(56) References Cited

U.S. PATENT DOCUMENTS

| | | |
|---|---|---|
| 6,294,063 B1 | 9/2001 | Becker et al. |
| 2002/0022276 A1 | 2/2002 | Zhou et al. |
| 2006/0205093 A1 | 9/2006 | Prins |
| 2007/0097333 A1* | 5/2007 | Zavarehi ............... G03B 21/20 353/85 |

FOREIGN PATENT DOCUMENTS

| | | |
|---|---|---|
| CN | 1267089 A | 9/2000 |
| WO | 2008102218 A1 | 8/2008 |
| WO | 2009007797 A1 | 1/2009 |

OTHER PUBLICATIONS

Luxton et al, "Use of External Magnetic Fields to Reduce Reaction Times in an Immunoassay Using Micrometer-Sized Paramagnetic Particles As Labels (Magnetoimmunossay)", Analytical Chemistry, 2004, vol. 76, No. 6, pp. 1715-1719.

* cited by examiner

Primary Examiner — Robert Xu

(57) ABSTRACT

A biosensor device controls actuation of label particles e.g., using frustrated total internal reflection. By applying a predetermined actuation force on the label particles and determining the effect of the applied actuation force in a binding volume or surface of a sensor cartridge of the biosensor device, a feedback control of the actuation force is applied.

14 Claims, 2 Drawing Sheets

MAGNETIC BEAD ACTUATION USING FEEDBACK FOR FTIR BIOSENSOR

CROSS REFERENCE TO RELATED APPLICATIONS

This application is a divisional of U.S. application Ser. No. 12/865,864 filed Aug. 3, 2010, know U.S. Pat. No. 8,822,227), which is a national filing of international application serial no. PCT/IB2009/050396, filed Feb. 2, 2009, which claims the benefit of EP application serial no. 08101328.6 filed Feb. 6, 2008, all of which are incorporated herein by reference.

FIELD OF THE INVENTION

The invention relates to a biosensor device, such as a biosensor device using frustrated total internal reflection (FTIR).

BACKGROUND OF THE INVENTION

The demand for biosensors is increasingly growing these days. Usually, biosensors allow for the detection of a given specific molecule within an analyte, wherein the amount or concentration of said target molecule is typically small. For example, the amount of drugs or cardiac markers within saliva or blood may be measured. Drugs-of-abuse are generally small molecules that only possess one epitope and for this reason cannot be detected, e.g., by a sandwich assay. A competitive or inhibition assay is a preferred method to detect these molecules. A well-known competitive assay setup is to couple the target molecules of interest onto a surface, and link antibodies to a detection tag, that may be an enzyme, a fluorophore or magnetic beads. This system is used to perform a competitive assay between the target molecules from the sample and the target molecules on the surface, using the tagged antibodies. For road-side testing, the assay should be fast so that a test may be performed in about 1 min, and robust.

Generally, a biosensor device using frustrated total internal reflection (FTIR) comprises a sensor device in which a sensor cartridge is to be inserted. The sensor cartridge comprises a sensor chamber wherein at least a portion of a sensor surface or volume in said sensor chamber is prepared for the detection of the target molecules. Usually, the sensor surface includes various binding spots. The sensor cartridge may be a disposable polystyrene cartridge. Paramagnetic beads are arranged in the sensor chamber. To increase the reaction speed of target molecules in a liquid which is inserted into the sensor chamber, actuation means, such as actuation coils, are arranged below the cartridge to generate an actuation force to pull the beads towards the sensor surface. After a predetermined time, which should be sufficient for the beads to bond on the binding spots, the lower coil is switched off and thus the actuation force is removed. In order to pull the non-bonded beads away from the sensor surface, another magnetic field may be applied which is generated by another coil arranged above the cartridge. Subsequently, the presence of beads at the binding spots on the sensor surface may be detected. Usually, a predetermined coil current is applied to the coils in order to generate a predetermined magnetic field. The magnetic force applied by the coils may also be used to further manipulate the assay.

In a FTIR sensor device, a camera, preferably a CCD or a CMOS camera, may be used to image the light reflected from the sensor surface and to observe the binding on the binding spot on the sensor surface. A typical picture obtained with a FTIR biosensor device is shown in FIG. 1. In FIG. 1, the image of a sensor surface 11 is shown, the surface 11 comprising various binding spots $A_1$, $A_2$ which are surrounded by a white area $B_1$ and $B_2$. The pictures are obtained by substantially homogeneously illuminating the sensor surface 11 and projecting the reflected light via an optical system to the camera. The relative darkening of a binding spot, for example binding spot $A_1$, compared to the surrounding white area $B_1$ is a measure for the number of bindings. In FIG. 1, the situation is shown where the relative darkening of spot $A_1$ is greater than the relative darkening of spot $A_2$. FIG. 1 further shows alignment marks 10 which define the positions of the binding spots.

Even thought the coil currents, and thus the generated magnetic field, may be controlled in a precise and reproducible way, the effect of the magnetic actuation applied on the magnetic beads depends on various parameters. For example, the assays may degrade over time which may change the composition of the matrix and the magnetic properties of the beads. The positioning of the cartridge in the reader and also the positioning of the actuation coils with respect to the cartridge and the binding spots may also change due to production tolerances when manufacturing the reader device and cartridge. The viscosity of the liquid applied to the sensor cartridge may vary since, e.g., different saliva samples which may be used, may have different viscosity. Moreover, the strength and quality of the chemical bindings may vary. For example, especially when measuring in blood, fragile bindings may occur, so that too low coil-currents will decrease the effect of the actuation, while too large currents may break the bindings or form clusters when non-bonded beads are to be pulled away from the sensor surface. The above-mentioned parameters may also vary depending on the temperature of the sensor device which may particularly change when the device is used for road-side testing. These parameters, which may strongly influence the magnetic actuation applied on the magnetic beads in the sensor cartridge, are difficult and expensive to control.

SUMMARY OF THE INVENTION

There is therefore a need to provide a method and a device for controlling and possibly optimizing the effect of actuation, in particular magnetic actuation, on label particles in a biosensor device. Specifically, the effect of parameters which influence the actuation, such as the parameters mentioned above, should be reduced or avoided.

According to the present invention, the force for actuating the label particles is controlled based on a determination of the effect of the applied actuation force in the binding volume or surface of a sensor cartridge of a biosensor device. Thus, a feedback control may be implemented. In case the binding volume or surface is analyzed optically, such as in a FTIR biosensor device, the feedback loop may comprise optical imaging and magnetic actuation. The magnetic actuation force may be controlled by controlling the coil currents or by controlling the positioning of the coil relative to the sensor cartridge. Furthermore, when a plurality of coils is used, also the geometric shape of the magnetic field may be controlled in order to influence the magnetic actuation and steer beads to a particular area of the sensor.

When the analysis of the binding volume or surface is done by observing the binding volume or surface with a camera, such as a CCD, the analyzing step may include real-time image processing to obtain enough control bandwidth and gain. Alternatively, determining the effect of the applied actuation force in the binding volume or surface may be performed by observing optical spots or using magnetic sensors, such as GMR or AMR, in order to obtain the parameters necessary to control the actuation force. The method may further be used in combination with any known detection method, such as magnetic or optical methods as mentioned above, in combination with any label particles or target molecules which may be actuated, for example in a magnetic or electrical way, using the Hall-effect, by flow or pressure or any other actuation means.

The invention further provides a device which is particularly adapted to perform the method according to the invention.

With the method and the device according to the invention, the influence of many assay parameters, which may otherwise hamper a correct measurement, may be reduced and the robustness of the biosensor may be enhanced significantly, especially when used under varying conditions like road-side drugs-of-abuse tests.

These and other aspects of the invention will be apparent from and elucidated with reference to the embodiments described hereafter.

DETAILED DESCRIPTION OF EMBODIMENTS

Figure 2:
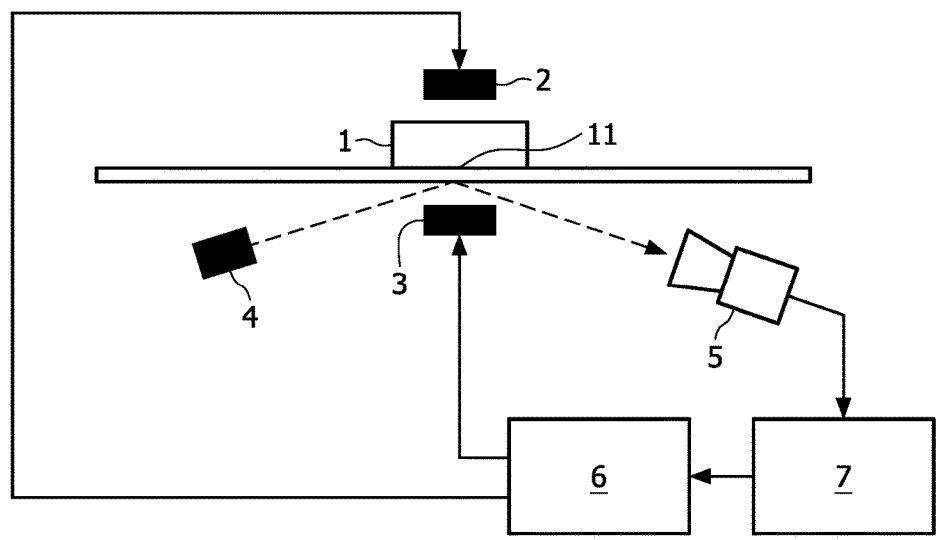
FIG. 2 schematically shows a set-up for a FTIR biosensor device according to an embodiment of the present invention.

According to an embodiment of the present invention, a FTIR biosensor device as illustrated in FIG. 2 may be used. The device includes a sensor cartridge 1 which may be removable from the biosensor device. In the sensor cartridge, a sensor chamber including appropriately prepared magnetic beads is provided. The biosensor device further comprises a light source 4, such as a laser diode or LED, for generating a light beam which illuminates a binding surface 11 of the biosensor cartridge under an angle which fulfills the requirements for total internal reflection. The light reflected from the sensor surface 11 is detected by a detection means 5, such as a photo-diode or a camera, e.g. a CCD.

In order to increase the reaction speed of the magnetic beads, a magnetic actuation coil 3 is arranged below the cartridge 1 facing the sensor surface, to generate a magnetic field to pull the beads towards the sensor surface 11. A further magnetic coil 2 may be arranged above the cartridge to pull the beads, which, after a predetermined time, do not establish a bonding with the binding areas on the sensor surface 11, away from the sensor surface 11. I.e., in this so-called washing step, un-specified and un-bonded beads may be removed from the sensor surface 11, in order to avoid any perturbation of the measurement caused by beads which accidentally are arranged close to the sensor surface 11.

The force required to pull the non-bonded beads away from the sensor surface in the washing step is very critical to tune. It is particularly difficult to find a balance between washing sufficient beads away from the sensor surface 11 while not breaking the fragile bindings between the sensor surface 11 and the bonded beads. The effect of a relatively small wash-current in a coil 2 may be observed and processed in real-time by analyzing the image observed by camera 5. This may be done by connecting the output of the CCD camera 5 with a video interpreter 7 and controlling the actuation coils 2, 3 using an actuation driver 6 in response to the output of video interpreter 7. Video interpreter 7 and actuation driver 6 may be implemented by a computer.

Figure 1:
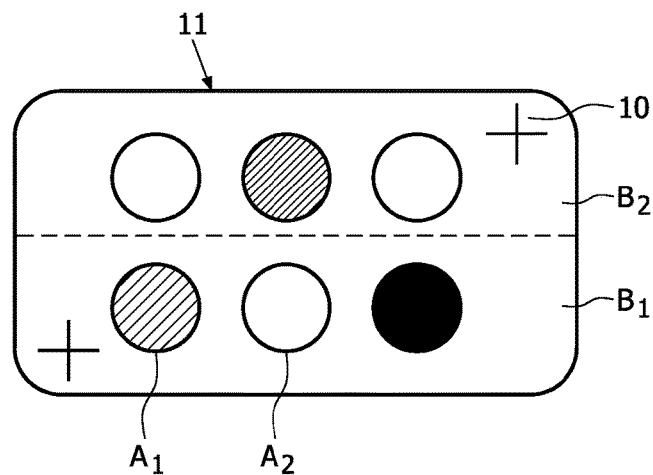
FIG. 1 shows an image observed in a FTIR biosensor device.

When the current in coil 2 is increased, the washing of the beads, i.e., pulling the non-bonded beads away from the sensor surface 11, gradually takes place, which again may be simultaneously observed in real-time. The effect of the applied current may be observed even more precisely by observing the effect in both, the binding-areas, i.e. the binding spots $A_1$, $A_2$, and non-binding areas, such as areas $B_1$, $B_2$ as shown in FIG. 1.

With this embodiment of the present invention, the actuation force needed to reliably remove only non-bonded beads from the sensor surface 11 may be performed by real-time observing the sensor surface 11 and, based on this observation, controlling the actuation force, i.e. the magnetic force applied by actuation coil 2.

The above-described process to selectively control the actuation force acting on the beads in the sensor cartridge 1 may also be used to determine the quality of the chemical bindings of the beads on the binding spots on the sensor surface 11. This may be done by increasing the wash-current in actuation coil 2 until also bonded beads disappear from the sensor surface 11, thereby effectively breaking or stretching the bindings. The result of such a measurement may be used as a measure of the reliability of the assay.

Figure 3:
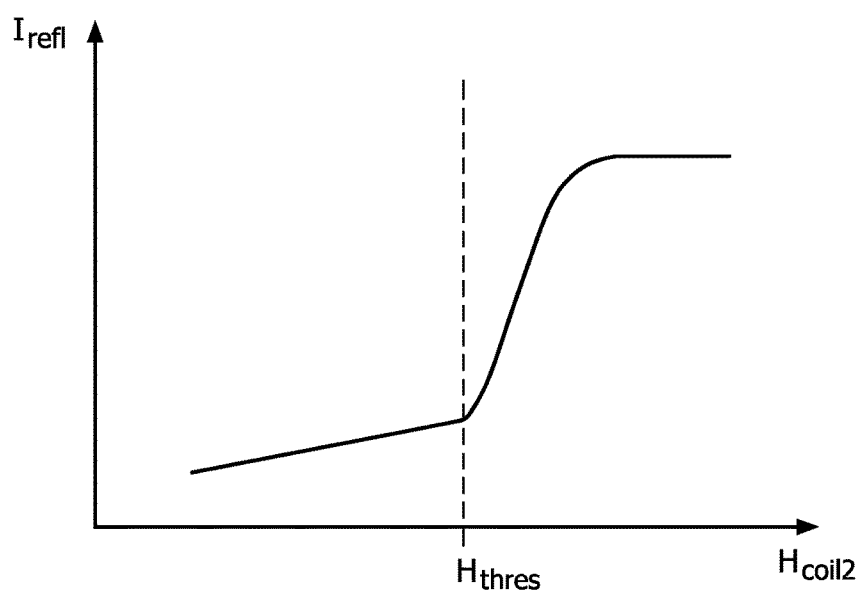
FIG. 3 shows a diagram of a signal observed in a FTIR biosensor as a function of the magnetic actuation field.

FIG. 3 shows a schematic diagram of the magnetic field generated by actuation coil 2 as a function of the intensity observed in a FTIR biosensor device. At low magnetic fields, the intensity increases slowly with an increasing magnetic field. This reflects the removal of the non-bonded beads from the sensor surface 11. From a certain threshold indicated with $H_{thres}$, also bonded beads are pulled away from the sensor surface 11. Accordingly, the reflected intensity observed in the FTIR biosensor device increases until substantially all beads are removed from the sensor surface 11. Accordingly, from a certain magnetic field, the intensity remains substantially constant. Such a measurement may be used to determine the magnetic field required to remove substantially all non-bonded beads as fast as possible from the sensor surface. I.e., in order to reliably remove only non-bonded beads, the magnetic field of actuation coil 2 should be kept below $H_{thres}$.

The principle of the above-described embodiment of the present invention may be extended to various applications. For example, attracting beads to the sensor surface 11 using actuation coil 3 in order to facilitate the binding of the beads to the binding spots on the sensor surface 11 may be optimized by observing the beads on the sensor surface 11 and controlling the actuation in such a way that unspecific bindings and clusters are avoided. Furthermore, by applying coil-currents alternately to both actuation coils 2 and 3 and, simultaneously, observing the position of the beads in the sensor chamber, the beads may be moved across the sensor chamber or sensor surface 11 in a predetermined way, in order to steer and mix a liquid in the sensor chamber.

With the device and method of the present invention, an increased assay robustness may be achieved by reducing the effect of various assay tolerances, which is especially important for road-side drug testing. Furthermore, the production tolerances when manufacturing biosensor devices and in particular sensor cartridges and thus the production price may be reduced. The present invention offers an optimal balance between hardware and software processing needed in a biosensor device, in particular a FTIR biosensor device.

While the invention has been illustrated and described in detail in the drawings and foregoing description, such illustration and description are to be considered illustrative or exemplary and non-restrictive; the invention is thus not limited to the disclosed embodiments. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage. Any reference signs in the claims should not be considered as limiting the scope.

The invention claimed is:

1. A biosensor device comprising:
    a sensor chamber comprising a binding surface for binding label patricles;
    an actuator configured to apply a magnetic field to the sensor chamber to generate a predetermined actuation force for actuating the label particles;
    a light source configured to project light onto the binding surface;
    a photodetector configured to receive light from the binding surface;
    a computer programmed to:
        from the light received by the photodetector, determine a magnetic field threshold ($H_{thres}$) at which a slope of a plot of light intensity reflected from the binding surface versus the applied magnetic field increases and is no longer substantially constant; and
        during detection of target molecules, control the actuator to apply a magnetic field to the sensor chamber which is at or below the magnetic field threshold ($H_{thres}$) to remove unbound particles from the binding surface.

2. The biosensor device according to claim 1, wherein said actuator comprises electromagnetic actuation coils.

3. The biosensor device according to claim 1, wherein the computer is further programmed to control the applied magnetic field to the sensor chamber by controlling a current in actuation coils that apply the magnetic field.

4. The biosensor device according to claim 1, wherein the computer is further programmed to control the applied magnetic field to the sensor chamber by controlling a position of actuation coils that generate the magnetic field with respect to the sensor chamber.

5. The biosensor device according to claim 1, wherein the photodetector is configured to detect light scattered from the binding surface.

6. The biosensor device according to claim 1, wherein the biosensor device includes a frustrated total internal reflection (FTIR) magnetic biosensor device.

7. The biosensor device according to claim 1, wherein the computer is further programmed to determine when the slope is no longer substantially constant based on light received from non-binding areas of the sensor chamber.

8. The biosensor device according to claim 7, wherein the computer is further programmed to simultaneously determine the slope in real-time based on the light received from the binding surface and the non-binding areas of the sensor chamber.

9. The biosensor device according to claim 1, wherein the computer is further programmed to control the applied magnetic field to the sensor chamber to remove only non-bonded label particles from the binding surface based on real-time observation of the binding surface for determining an effect of the applied magnetic field to the sensor chamber at the binding surface.

10. The biosensor device according to claim 1, wherein the computer is further programmed to increase a force directed away from the binding surface until bonded label particles leave the binding surface and the computer is further programmed to determine a quality of the binding of the label particles to the binding surface.

11. A Frustrated Total Internal Reflection (FTIR) biosensor device, comprising:
    a sensor cartridge having a binding volume or surface and configured to receive a plurality of label particles;
    coils configured to apply a magnetic field to the sensor cartridge to generate an actuation force for actuating the plurality of the label particles;
    a light source configured to project light to the binding volume or surface;
    a photodetector configured to image light reflected from the binding volume or surface;
    a computer programmed to:
        control the coils to increase a magnetic field applied to the sensor cartridge from a low strength and control the light source to project light on the binding surface;
        as the applied magnetic field increases, analyze an intensity of the reflected light to identify a threshold value ($H_{thres}$) for the magnetic field at which the intensity of the reflected light versus the magnetic field becomes no longer substantially constant, and
        to remove unbound particles from the sensor surface during a subsequent measurement, control the magnetic field applied by the coils so that the applied magnetic field is below the identified threshold value $H_{thres}$.

12. The biosensor device according to claim 11, wherein the $H_{thres}$ identifies the strength of the magnetic field which is required to remove substantially all label particles which are not bound to the binding volume or surface of the sensor cartridge without removing label particles which are bound to the binding volume or surface.

13. The biosensor device according to claim 11, wherein the photodetector is configured to image the light in real-time and the computer is further programmed to analyze the intensity of the imaged light.

14. A biosensor device controlling actuation of label particles in a biosensor device having a sensor chamber including a binding surface for binding the label particles, the biosensor device comprising:
    means for applying a magnetic field to the sensor chamber to generate a predetermined actuation force for actuating the label particles;
    means for applying an increasing magnetic field to the sensor chamber to increase a force, urging the particles away from the binding surface;
    means for determining when a slope of a plot of light intensity reflected from the binding surface versus the applied increasing magnetic field is no longer substantially constant by projecting a light onto the binding surface and imaging a reflection of the light as the applied magnetic force increases; and means for controlling the applied magnetic field to a strength below a point on the plot at which the slope is no longer substantially constant to remove unbound particles from the binding surface.

\* \* \* \* \*